United States Patent
Turovets et al.

(10) Patent No.: US 11,744,856 B1
(45) Date of Patent: Sep. 5, 2023

(54) COMPOSITIONS AND METHODS TO IMPROVE SKIN QUALITY AND APPEARANCE, CURE SKIN AND TISSUE DAMAGE, AND USE IN THERAPY

(71) Applicant: MediCell Technologies, Inc., Carlsbad, CA (US)

(72) Inventors: Nikolay Turovets, Carlsbad, CA (US); Christopher B. Adams, Los Angeles, CA (US)

(73) Assignee: MediCell Technologies, LLC, Carlsbad, CA (US)

( * ) Notice: Subject to any disclaimer, the term of this patent is extended or adjusted under 35 U.S.C. 154(b) by 0 days.

(21) Appl. No.: 15/701,198

(22) Filed: Sep. 11, 2017

Related U.S. Application Data

(62) Division of application No. 13/858,654, filed on Apr. 8, 2013, now abandoned.

(60) Provisional application No. 61/622,855, filed on Apr. 11, 2012.

(51) Int. Cl.
 *A61K 35/12* (2015.01)

(52) U.S. Cl.
 CPC .................... *A61K 35/12* (2013.01)

(58) Field of Classification Search
 None
 See application file for complete search history.

(56) References Cited

U.S. PATENT DOCUMENTS

| | | | |
|---|---|---|---|
| 7,118,746 B1 * | 10/2006 | Naughton | A61K 8/02 |
| | | | 424/184.1 |
| 8,361,485 B2 | 1/2013 | Naughton et al. | |
| 2009/0202654 A1 * | 8/2009 | Nixon | A61K 8/985 |
| | | | 424/574 |
| 2012/0189687 A1 | 7/2012 | Johnson | |
| 2012/0195969 A1 | 8/2012 | Riordan et al. | |
| 2012/0219634 A1 | 8/2012 | Maslowski et al. | |
| 2012/0225029 A1 * | 9/2012 | Al-Qahtani | A61K 38/08 |
| | | | 424/85.2 |
| 2012/0230940 A1 | 9/2012 | Naughton et al. | |
| 2012/0276215 A1 | 11/2012 | Riordan et al. | |
| 2013/0058903 A1 | 3/2013 | Lee | |

FOREIGN PATENT DOCUMENTS

| | | | |
|---|---|---|---|
| EP | 2554175 | 2/2013 | |
| JP | 5138129 | 11/2012 | |
| WO | WO-0114527 A1 * | 3/2001 | ............... A61K 8/99 |
| WO | WO-2011127090 A1 * | 10/2011 | ............. A61P 17/02 |
| WO | 2012/065121 | 5/2012 | |
| WO | 2012/121695 | 9/2012 | |

OTHER PUBLICATIONS

Davis et al. "Nanoparticle therapeutics: an emerging treatment modality for cancer", Nature Reviews 7: 771-82, 2008 (Year: 2008).*

Pellegrini, G. et al., "p63 identifies keratinocyte stem cells", PNAS, Mar. 13, 2001, 3156-3161, vol. 98, No. 6.

* cited by examiner

*Primary Examiner* — Emily A Cordas
(74) *Attorney, Agent, or Firm* — Fish IP Law, LLP

(57) ABSTRACT

Pharmaceutical and cosmetic compositions and methods are presented that have a carrier in combination with a media composition that is derived from distinct cell cultures. The distinct cell cultures are obtained from growing different cells that are distinct with respect to at least one of cell type, cell age, cell differentiation stage, and physiological condition. Thus, the composite medium will provide mediator molecules that are ordinarily not founds in their combination and that can be fine tuned to specific purposes.

10 Claims, 2 Drawing Sheets

US 11,744,856 B1

COMPOSITIONS AND METHODS TO IMPROVE SKIN QUALITY AND APPEARANCE, CURE SKIN AND TISSUE DAMAGE, AND USE IN THERAPY

This application is a divisional of U.S. application Ser. No. 13/858,654, which was filed Apr. 8, 2013 and claims priority to our US provisional application with the Ser. No. 61/622,855, which was filed Apr. 11, 2012, and both of which are incorporated by reference herein.

FIELD OF THE INVENTION

The field of the invention is cosmetic and pharmaceutical formulations and methods to improve skin quality (e.g., via ameliorating of the circulation of blood in the skin), particularly to reduce wrinkles, skin laxity, and facial fine lines, to reconstruct the structure of skin collagen, to restore cellular membranes of skin cells, to improve skin elasticity and/or to soften skin. The present invention also relates to formulations and methods to facilitate and accelerate wound healing, to treat burns and other tissue damage, preferably by stimulating the patient's own cells.

BACKGROUND OF THE INVENTION

During normal embryo development progenitor/stem cells release into their environment extracellular matrix proteins and regulatory stimuli such as growth factors, cytokines, and chemokines. These released molecules are thought to guide further organism/tissue development, stimulate cell specification and differentiation into particular cell types, direct tissue building and promote cell maturation. Moreover, the released factors also have critical biological activities, including angiogenetic, anti-scarring, chemo-attractant, supportive, anti-apoptotic, and immunomodulatory activity, and can therefore be considered as unique active elements with the potential to stimulate regeneration and repair of various tissues, and particularly skin.

Some of the release molecules were already proposed as ingredients in skin therapies and exemplary treatments are discussed in, for example, EP2554175, JP5138129, WO2012/065121, WO2012/121695, US2012/0189687, US2012/0195969, US2012/0219634, US2012/0230940, US2012/0276215, and US2013/0058903, all of which are incorporated by reference herein. However, to this date and to the best of the inventors' knowledge, there is no approach known in the art that has taken advantage of comprehensive in vivo use of such factors produced throughout the entirety of differentiation and/or maturation. Therefore, there is still a need to provide improved compositions and methods that benefit from factors produced throughout the entirety of differentiation and/or maturation.

SUMMARY OF THE INVENTION

The inventive subject matter is drawn to various compositions and methods in which a plurality of mediator molecules released from one or more cells are provided, typically in a form suitable for topical application.

It is especially preferred that the mediator molecules are derived from multiple cells and are a collection of mediator molecules where the cells are of (a) distinct cell type, (b) distinct cell age, (c) distinct cell differentiation stage, and/or (d) distinct physiological condition (e.g., same or different type of cells that could be healthy, infected, metabolically and/or environmentally challenged). Most typically, such collection of mediator molecules is based on a combination of distinct conditioned media of the cells. In especially preferred aspects of the invention, the cells are mammalian (typically adult) stem cells and their respective downstream progeny.

Consequently, pharmaceutical and cosmetic compositions and methods are contemplated that provide a comprehensive set or desired subset of factors and/or growth mediators to a mammal in need thereof. For example, it is known that stem cells, lineage committed cells, and progenitor cells release into their environment (e.g., culture medium) numerous unique factors during growth/expansion in vitro, during the course of in vitro differentiation and/or maturation. It is now contemplated that culture medium (CM) collected from growing cell cultures and/or collected cells during the whole cycle of differentiation/maturation (or during at least two distinct stages) will essentially contain the same and unique set of the growth factors and other regulatory molecules (including cytokines and chemokines) than tissue undergoing repair and/or restructure, and can therefore be used as a regenerative and stimulating agent for the skin and tissue repair after trauma (and especially wounds and burns).

Consequently, especially contemplated composition will include a carrier for topical application (e.g., formulated as a cream, a spray, or a balm) in combination with a multi-stage cultivation medium in a cosmetically, therapeutically, or prophylactically effective amount to treat or prevent a skin condition. The term "multi-stage cultivation medium" as used herein refers to a combination of growth media harvested from distinct cultures of distinct cell types, distinct cell ages, distinct cell differentiation stages, and/or distinct physiological condition. Moreover, such multi-stage cultivation medium may be as harvested, or may be processed for remove one or more undesired components. For example, suitable processing steps include filtration (e.g., to remove cells, debris, platelets, exosomes, and/or bacteria, and/or viruses, etc.), heat treatment (e.g., to heat inactivate potential pathogens, coagulate and remove certain proteins, etc.), chromatographic steps (e.g., affinity, size exclusion, ion exchange, etc.), salt fractionation, etc. Of course, it should be noted that the particular composition and combination of media will predominantly depend on the desired purpose, and that all reasonable combinations of media harvested from distinct cultures of distinct cell types, distinct cell ages, distinct cell differentiation stages, and/or distinct physiological condition are deemed suitable for use herein.

Based on the presence of a plurality of growth and differentiation factors produced from differentiating cells over a plurality of differentiation/maturation stages, the inventors now contemplate application a plurality of mediator molecules to ageing skin, a wound, or a burn as particularly desirable to so help restore a healthy and/or regenerated treated tissue. Most preferably, and to obtain the widest range of therapeutically or prophylactically effective molecules, the multi-stage cultivation medium is collected over at least two, more preferably at least four, and most preferably all differentiation stages of cultivated cells. Thus, it should be recognized that the multi-stage cultivation medium is most preferably collected from a cell culture that has originated from and included a stem cell, a germ line lineage committed cell, or a progenitor cell.

Among other beneficial uses of contemplated compositions and methods, it is generally contemplated that skin conditions particularly responsive to treatment with contemplated compositions and methods include wrinkles, skin laxity, facial fine lines, degraded skin collagen, degraded cellular membranes of skin cells, scarring, and/or reduced skin elasticity. Similarly, advantageous results are expected where the skin condition has undergone a traumatic event, including a cut, a bruise, a sore, an ulcer, and/or a post-operative trauma, or where the skin was subject to a sun burn, a second degree burn, and/or a third degree burn.

In still further preferred aspects, all or selected active mediator molecules are released by stem cells and cells subsequently differentiated therefrom, and are preserved and delivered on and/or into tissue (and especially skin) via nanoparticles (NP). For example, especially suitable particles include plant originated oleosomes or phospholipid-based liposomes. Thus, in yet another preferred aspect, NP containing contemplated composition can be added as an active or supporting ingredient into topical skin care products, therapeutic compositions, and prophylactic formulations.

Various objects, features, aspects and advantages of the inventive subject matter will become more apparent from the following detailed description of preferred embodiments.

DETAILED DESCRIPTION

Figure 1:
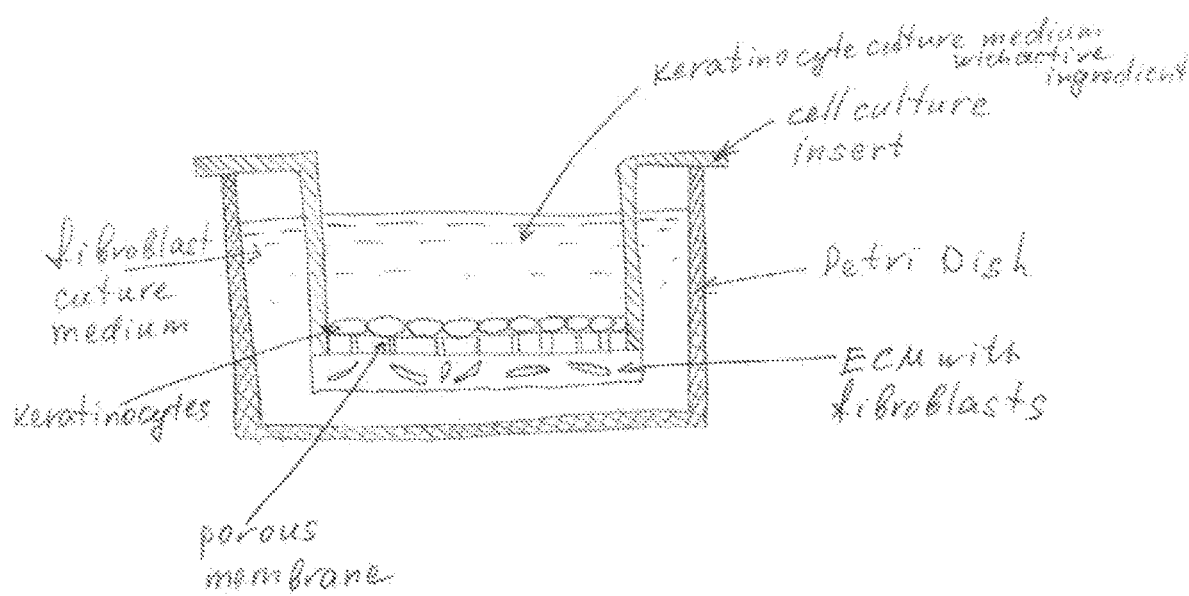
FIG. 1 is a schematic illustration of a cell culture to investigate effects of conditioned medium.

The inventors have now discovered that numerous compositions and methods may take advantage of selectively produced (and typically excreted) mediator molecules that are released from cells to so enable treatment and treatment modalities that will assist in repair, healing, and restructuring processes of previously injured tissues. Moreover, contemplated compositions and methods are also thought to exhibit significant prophylactic uses, particularly in dermatological applications.

In general, contemplated compositions will include a plurality of mediator molecules that are produced by and removed from cells of distinct cell type, distinct cell age, distinct cell differentiation stage, and/or distinct physiological condition. In most instances, the compositions presented herein will comprise a collection of mediator molecules from at least two, more typically at least three, and even more distinct cell culture media, wherein the medium may be further processed to further enrich medium for one or more of the mediator molecules.

With respect to suitable cells it is contemplated that numerous types of cells are deemed appropriate for use herein, and especially those that are not fully differentiated cells and undergo at least one differentiation and/or maturation step (e.g., characterized by specific change in cellular epitopes, intracellular components, and/or expression pattern of one or more genes). For example, especially suitable stem cells include pluripotent stem cells including embryonic stem cells, induced pluripotent stem cells, parthenogenetic stem cells, and/or germ-derived stem cells. Additionally contemplated cells include adult stem cells, including mesenchymal stem cells, neural stem cells, retinal progenitor cells, and/or neural progenitor cells, and progenitor cells, including progenitor cells of skin types and/or cardiomyoblasts. While not particularly preferred, it is also contemplated that hybridoma and teratoma cells may be used in conjunction with the teachings presented herein. Likewise, embryonic stem cells are not excluded, however, not preferred for use herein.

It should further be recognized that where stem cells are used, it is particularly preferred that the cells have a differentiation direction that is similar or identical to the intended use. Thus, particularly contemplated stem cells for topical and dermal use will tend to differentiate into skin fibroblasts, keratinocytes, endothelium, and/or skin cell lineages. Therefore, and viewed from a different perspective, stem cells may be induced in an appropriate medium such that the cells will differentiate into any cell type of the mesoderm lineages, any cell type of the ectoderm lineages, any cell type of the endoderm lineages, and/or extra-embryonic lineages. Consequently, stem cells may also differentiate, inter alia, into neurons, cardiomyocytes, glia, astrocytes, retinal cells, corneal cells, trofectoderm and/or placental cell types. Further particularly preferred cells include skin stem cells, epidermal stem cells, germ derived stem cells, skin-resident stem cells, hair follicle stem cells, Lgr6-expressing cells, bulge stem cells, epidermal stem cells. Where the cells are progenitor cells, the following cell types are especially preferred: Skin progenitor cells, fibroblast progenitor cells, keratinocyte progenitor cells, muscle progenitor cells, epithelial progenitor cells, mesothelial progenitor cells, endothelial progenitor cells, fat progenitor cells, epidermal progenitor cells, retinal progenitor cells, satellite cells, neural progenitor cells, intermediate progenitor cells, bone marrow stromal cells, periosteum progenitor cells, pancreatic progenitor cells, angioblasts, myoblasts, embryonic progenitor cells, hair follicle progenitor cells, sebocyte progenitor cells, and melanocyte progenitor cells.

Of course, it should be recognized that numerous approaches for cell differentiation are deemed appropriate, and contemplated approaches include directed differentiation approaches that utilize special differentiation conditions, growth factors, special media, genetic modification, and/or spatially structured 3-D environments (nanopost culture base, tissue matrix support, etc.) etc. Alternatively, or additionally, spontaneous differentiation approaches may be employed that utilize factors withdrawn from the culture media that support the keeping of undifferentiated stage of the progenitor/stem cells.

Of course, it should be noted that while stem cells are generally preferred, various non-stem cells may also be used as sole cell type, or in combination with stem cells. Most preferably, the non-stem cells are of the same species (preferably mammal, most preferably human), but it should be appreciated that cells of different species are also appropriate. It is also preferred that the cells will be primary cells or descend from cryopreserved cells, however, immortalized cells are also deemed suitable for use herein. For example, while one culture medium may be derived from mammalian adult stem cells, another culture medium may be derived from murine or canine fibroblast cells. Thus, suitable cells may be derived from any source and species, living or preserved, native, or immortalized. Additionally, it should be appreciated that suitable cells may be derived from the person that is to be treated, or from an allogenic or even xenogenic source. Thus, and viewed from yet another perspective, cells contemplated herein may be from an already established cell culture, or from a primary tissue/cell culture (which may be initiated for cell culture, for example, tissue digested and isolated cells seeded into cell culture ware). Of course, such cells may be supplemented with further cells from culture and/or other donors.

Regardless of the type and origin of the distinct cells it is generally preferred that the cells will be at distinct differentiation stages. For example, where the cells are of a human dermal cell type, the distinct cells may be human mesodermal stem cells and human fibroblasts. Likewise, and especially where the same type of cells are used (e.g., all stem cells, or all fibroblasts), it is generally preferred that the cell cultures will contain cells of different ages (e.g., one culture has cells having undergone less than 5 divisions, while another culture has senescent cells). With respect to cell age, it should be appreciated that the age can be determined/controlled by culture time, chronologic age, age as measured by telomere length, etc.

In yet further contemplated aspects, the cells may also be different in that they are distinct with respect to their physiological condition. For example, a first culture may contain cells that are optimally fed with a complete media composition, while another cell culture is subjected to metabolic stress (e.g., malnutrition, hyper/hypoglycemic conditions, oxidative stress, etc.), environmental stress (e.g., irradiated with ionizing radiation, electromagnetic radiation, UV light, etc.), and/or pathogen exposure (e.g., bacterial or viral infection, exposure to toxins, etc.)

Depending on the type of cells, differentiation approach, and culture conditions, it should be recognized that the schedule for collection of the cell medium may vary considerably. For example, suitable schedules include semi-continuous collection of medium from differentiating cells at regular intervals (e.g., twice weekly, every other day, every day, every half of day, every hour, etc.) or continuous collection (e.g., based on media flow in a bioreactor). Alternatively, media can also be collected during the whole cycle of differentiation (typically during a time period that lasts at least 1 hour).

Consequently, the type of media collection will also vary considerably. For example, in one approach, medium may be collected into a large vessel that is kept frozen (e.g., temperature range −5° C. to −196° C.), and newly collected medium is added into this vessel. Upon termination of the differentiation/maturation period, the contents are thawed and compounded with other components for the preparation of skin care compositions. In another approach, individual samples of the medium are collected, frozen, and stored in separate vessels (e.g., temperature range −5° C. to −196° C.). For example, one could freeze each sample of culture medium of a stem cell cultivation leading to differentiated cells and store the collected medium frozen (e.g., −5° C. to −196° C.). Upon termination of the differentiation/maturation and collection period, the frozen and collected contents are then thawed, combined, and compounded with other components for the preparation of contemplated compositions, and most typically skin care compositions. Regardless of the type and manner of collection, it should be recognized that the conditioned medium is preferably collected from cells cultured under current good manufacturing practice (cGMP) conditions.

In yet another aspect of the inventive subject matter, it should still further be appreciated that processing of the collected media may vary considerably, and the type of medium and ultimate formulation will at least in part determine the particular processing technique. Thus, all known techniques of processing are deemed suitable, including filtration, centrifugation, chromatographic processes, antibody precipitation, etc. However, it is generally preferred that the collected material is subjected to one or more clarification steps to remove debris. Moreover, and especially where selected mediator molecules have a known molecular size or association with a fraction of known size (e.g., carrier protein, exosome, lysosome, platelet, etc.). Therefore, processing will include at least one of removal of water, cellular debirs, subcellular organelles or compartments, etc. Viewed from another perspective, processing may also be used to selectively enrich in one or more mediator molecules, for example, via chromatographic steps, membrane separation, salt fractionation, dialysis, etc.

It is generally contemplated that the media preparations may be formulated into a variety of different formulations, and all known formulations (e.g., oral, parenteral, topical, etc.) are deemed suitable for use herein. However, it is especially preferred that the formulations are topical formulations suitable for application to intact skin and damaged/diseased skin. Thus, and among other suitable formulations, topical gels, creams, ointment, mousses, sponges, and powders, etc. are particularly preferred. Moreover, it should be appreciated that the media preparations may be included into the formulations as isolated, as processed (e.g., concentrated, dried, etc.), and/or in a specific formulation (e.g., in liposomes, nanosomes, etc.), and that the actual choice will at least in part be determined by the desired use and cell media.

For example, it is contemplated that the media (CM) that contain active ingredients (that are released by stem cells) are incorporated into nanoparticles including oleosomes and liposomes. These nanoparticles are then added to the skin care and/or therapeutic composition (CM/NP). For example, skin care compositions may be prepared from a base plus CM/NP (0.1%-20%), or from a base plus CM/NP (0.1%-20%) plus a supporting complex (e.g., vitamins (including B complex, C, E, D, P etc.), co-enzyme Q10, antioxidants, plant extracts, UVA sunscreen, UVB sunscreen, moisturizing factors, etc.). In other examples, various therapeutic compositions may be prepared from a base plus M/NP (0.1%-20%), or from a base plus CM/NP (0.1%-20%) plus a supporting complex (e.g., known factors stimulating wound or burn healing).

It is generally preferred that at least some of the collected media with the plurality of mediator molecules from different cells or cell stages is encapsulated in nanoparticles that are formed from lipid components. Especially preferred lipid components are membrane forming and most preferably lipids found in cell membranes of dermal cells. Depending on the particular lipid (composition) and manner of manufacture, it should therefore be appreciated that the nanoparticles may have a monolayer or bilayer membrane structure, and may be unilamellar or multi-lamellar structures. Additionally, the particles may be further modified with additional components that are displayed on the particle surface (e.g., antibodies or fragments thereof, or other affinity moieties, including Annexin V, hemagglutinin, etc.). Most typically, the nanoparticles will have a size between 10 and 5000 nm, and more typically between 50 and 500 nm. However, in alternative aspects, the nanoparticles may also be larger (or even smaller).

Likewise, it is contemplated that the nanoparticles may also be composed of materials other than lipids, and especially preferred alternative materials include various pharmaceutically acceptable polymers, which may be stable or biodegradable/bioerodable. For example, suitable polymers may include polylactic acid polymers, polyhydroxybutyrate polymers, etc. In such examples, the collected media with the plurality of mediator molecules from different cells or cell stages may be encapsulated to thereby form a filled vesicle, or may be admixed to thereby form a sponge-like structure. In still further suitable formulations, the collected media with the plurality of mediator molecules from different cells or cell stages may not be encapsulated or trapped in a solid or membranous carrier, but present as a distinct phase in a lipophilic carrier. For example, contemplated compositions and formulations may be an emulsion, microemulsions, oil-in-water and water-in-oil emulsion, multiphase mixture, etc.

Depending on the particular use and composition, it should be noted that the formulations will include varying quantities of the media preparation. However, it is generally preferred that the media preparation will be present in a relatively low amount, and suitable quantities are between 25 wt % to 10 wt %, between 10 wt % to 1 wt %, between 1 wt % to 0.1 wt %, and between 0.1 wt % to 0.01 wt %, and even less. Consequently, administration and treatment schedule will vary considerably. For example, for acute treatment of a burn or open wound, administration may be a single administration, once, twice, three times daily, and even administration under occlusion. On the other hand, where use is prophylactic cosmetic use, administration may be less frequent, such as once or twice weekly. Most typically, the type of use and media formulation will at least in part determine the dosage and frequency of administration.

It is generally contemplated that the compositions and methods presented herein are suitable for prophylactic and/or therapeutic use, and especially preferred uses are prophylactic use in the cosmetic and aesthetic field and therapeutic as treatment for various insults, including radiation, trauma, infection, etc. For example, contemplated uses will include topical application to the skin and/or damaged surface and surrounded tissues in therapeutically or prophylactically effective amounts.

In further preferred aspects of the inventive subject matter, contemplated compositions and formulations are used in treatment, prophylaxis, and cosmetic application, and most typically in topical format. For example, where contemplated compositions and formulations are used in treatment, it is generally preferred that all conditions are suitable that involve cell and/or tissue repair, restoration, and/or remodeling. Therefore, exemplary treatments will include treatment of mechanical, thermal, and/or irradiative insults, and especially mechanical trauma resulting in open wounds (e.g., bruises, scratches, tears, cuts, abrasions, tissue damage due to gunshot wounds, shrapnel, and/or other foreign debris), blunt force trauma (e.g., hematoma, bruises), solar and ionizing radiation resulting in burns of various degrees, etc. Therefore, it should be noted that the compositions and formulations presented herein will be used to induce, promote/accelerate, or assist in healing or repair of injured tissue, and/or used to stimulate resolution of bruises and hematomas.

As the inventors contemplate that the inventive compositions and formulations will assist in repair, restoration, and tissue regeneration/remodeling, it should be appreciated that such modes of action may be due to various processes, including recruitment of immune competent cells, recruitment of adult resident and/or circulating stem cells (which may or may not be further differentiated by the compositions), and endogenous tissue repair (e.g., via matrix proteinases and cellular resorption). Thus, it should be recognized that contemplated compositions and formulations may also be particularly effective in the reduction in scar formation, or reduction of existing (already formed) scar tissue, and may further ameliorate or increase circulation of blood in the treated skin and/or tissue (e.g., by neovascularization or formation of microcapillary networks).

Moreover, the stimulation of (or direct) restorative effect may also lead to a significant reduction of wrinkles, may stimulate expansion of subdermal adipose tissue, which in turn will lead to improved skin elasticity, extensibility and firmness, and reduced skin laxity. Moreover, contemplated compositions may be effective in increasing skin moisturization/hydration, and may increase skin barrier function (via additional cells or increased stratum corneum thickness), which will advantageously reduce transepidermal water loss. Consequently, and viewed form a more systemic perspective, contemplated compositions and methods will reduce facial fine lines, improve skin softening, skin color, skin tone, and skin color evenness.

While not wishing to be bound by any particular theory or hypothesis, the inventors contemplate that the compositions and formulations presented herein are particularly effective to (a) stimulate cell migration (especially including stem cells and immune competent cells) and/or reconstruction of skin collagen structure, (b) stimulate redistribution of cells in a damaged area and surrounded tissues, (c) inhibit apoptosis and/or stimulate angiogenesis and/or chemotaxis and/or activate immune response. Still further, contemplated compositions and formulations may also be effective in stimulation of repair of cellular membranes of various dermal cells. One of the possible contributing factors in the desired tissue repair and/or restructure may be due to various protein-based factors and degradation products thereof.

For example, various cells are known to release into the medium factors with anti-apoptotic activity (including VEGF, HGF, IGF-I, stanniocalcin-1, TGF-betta, bFGF, GM-CSF), molecules with immunomodulatory activity (including PGE-2, TGF-betta, HGF, mpCCl2, IDO, iNOS, HLA-G5, LIF), molecules with anti-scarring activity (including bFGF, HGF, adrenomedullin), molecules with supportive activity (including SCF, LIF, IL-6, M-CSF, SDF-1, angiopoietin-1), molecules with angiogenic activity (including bFGF, VEGF, PlGF, MCP-1, IL-6, extracellular matrix molecules), and/or molecules with chemoattractant activity (CCL2, CCL3, CCL4, CCL5, CCL7, CCL20, CCL26, CX3CL1, CXCL5, CXCL11, CXCL1, CXCL2, CXCL8, CCL10, CXCL12). Degradation products of such proteins may be due to natural proteolytic processes in the cell or extracellular space, but also due to non-specific protein degradation. Most notably, such degradation products are also deemed to have biological activity in the context of tissue repair and/or remodeling. Moreover, it should be appreciated that the cells may also release into the medium various proteins forming and/or associated with the extracellular matrix.

Additionally, or alternatively, it is contemplated that the conditioned medium (or cell secreted components of conditioned medium, or parts of cell secreted components of conditioned medium) will stimulate cell migration, expression of genes coding extracellular matrix proteins (including collagens, elastins, fibronectin), and/or stimulate expression of genes coding integrins and adhesion molecules. Moreover, the mediator molecules in the conditioned medium may also change the expression pattern of genes coding extracellular matrix proteins, activate endothelial cells, stimulate angiogenesis properties of the endothelial cells, stimulate proliferation of the cells (including endothelial cells, fibroblasts, keratinocytes), change metabolism of the cells (including endothelial cells, fibroblasts, keratinocytes), and/or stimulate release of growth factors, chemokines, and cytokines by cells (including endothelial cells, fibroblasts, keratinocytes).

EXAMPLES

Example 1. CM Collection

1. Plate human embryonic stem cells or human parthenogenetic stem cells on the plastic culture dish pretreated with human serum. The plating medium: Knock-out DMEM/F12 supplemented with 16% Xeno-Free Knockout Serum Replacement, 0.4% NEAA Solution, 0.9% GLUTAMAX-I™ (200 mM L-alanyl-L-glutamine in 0.85% NaCl) and 6 ng/ml recombinant human fibroblast growth factor 2.
2. Expose culture dishes with cells in the incubator under +37° C., 4.9% $CO_2$, humidified atmosphere within 75 hours. Change medium (the same as plating medium) 25 hours and 50 hours later after plating.
3. To initiate differentiation (75 hours later after plating) replace medium with differentiation medium: Knockout DMEM/F12 supplemented with 16% Xeno-Free Knockout Serum Replacement, 0.4% NEAA Solution and 0.9% GLUTAMAX-I™ (200 mM L-alanyl-L-glutamine in 0.85% NaCl), and further exposure culture dishes with differentiating cell cultures in the incubator under +37° C., 4.9% $CO_2$, humidified atmosphere within 21 days.
4. Collect medium (CM) from the differentiating cultures every 24 hours within 21 days. First collection should occur after 24 hours later after initiation of the application of differentiation medium. The last collection should occur 504 hours later after initiation of the application of differentiation medium. After each collection add fresh differentiation medium to the differentiating cultures.
5. Centrifuge CM under 400 g for 5 minutes.
6. Collect supernatant and keep it frozen −20° C.
7. After last CM collection, thaw all previously collected CM samples, mix it together and use for the CM/NP preparation.

Example 2. CM Collection

1. Plate human retinal progenitor cells on the plastic culture dish pretreated with fibronectin. The plating medium: DMEM/F12 supplemented with 0.9% N-2 Supplement, 0.9% GLUTAMAX-I™ (200 mM L-alanyl-L-glutamine in 0.85% NaCl) and 40 ng/ml recombinant human fibroblast growth factor 2.
2. Exposure culture dishes with cells in the incubator under +37° C., 4.9% $CO_2$, humidified atmosphere within 25 hours.
3. To initiate differentiation (25 hours after plating) replace medium with differentiation medium: DMEM/F12 supplemented with 0.9% N-2 Supplement, 0.9% GLUTAMAX-I™ (200 mM L-alanyl-L-glutamine in 0.85% NaCl) and 100 nM retinoic acid, and further exposure culture dishes with differentiating cell cultures in the incubator under +37° C., 4.9% $CO_2$, humidified atmosphere within 21 days.
4. Collect medium (CM) from the differentiating cultures every 24 hours within 21 days. First collection should occur after 24 hours after initiation of the application of differentiation medium. The last collection should occur 504 hours later after initiation of the application of differentiation medium. After each collection add fresh differentiation medium to the differentiating cultures.
5. Centrifuge CM under 400 g for 5 minutes.
6. Collect supernatant and keep frozen −20° C.
7. After last CM collection, thaw all previously collected CM samples, mix together and use for the CM/NP preparation.

Example 3. CM/NP Preparation

1. Mix 3 g of hydrogenated soybean lecithin with 50 ml distilled water and incubate 24 hours at room temperature.
2. Add 10 ml CM (from Example 1 or Example 2).
3. Mix 10 minutes.

The CM/NP is ready to use as component of skin care or treatment product.

Example 4. CM/NP Preparation

1. Mix 3 g of hydrogenated soybean lecithin with 30 ml distilled water and incubate 24 hours at room temperature.
2. Add 30 ml CM (from Example 1 or Example 2).
3. Mix 10 minutes.

The CM/NP is ready to use as component of skin care or treatment product.

Example 5. CM/NP Preparation

1. Mix 3 g of hydrogenated soybean lecithin with 60 ml CM (from Example 1 or Example 2) and incubate 24 hours at room temperature.
2. Mix 10 minutes.

The CM/NP is ready to use as component of skin care or treatment product.

Example 6. Differentiation Medium

Knockout-DMEM supplemented with 10% Xeno-Free Knockout Serum Replacement, 10% Plasmanate, 1% NEAA Solution, 1% GLUTAMAX-I™ (200 mM L-alanyl-L-glutamine in 0.85% NaCl), 01% beta mercaptoethanol.

Example 7. Exemplary Cosmetic Formulations

Contemplated media preparations as discussed above will be added to various cosmetic base formulations in proportions as given below:

1) Body Lotion (Oil-In-Water)

| | | |
|---|---|---|
| a) | PEG-7 hydrogenated castor oil | 2.00% |
| | PEG-20 glyceryl laurate | 1.00% |
| | cocoglycerides | 3.00% |
| | cetearyl alcohol | 1.00% |
| | cetearyl isononanoate | 4.00% |
| | octyl stearate | 4.00% |
| | phenoxyethanol, methylparaben, ethylparaben, butylparaben, propylparaben, isobutylparaben | 0.30% |
| b) | water, distilled | 73.40% |
| | phenoxyethanol, methylparaben, ethylparaben, butylparaben, propylparaben, isobutylparaben, | 0.30% |
| | glycerin | 3.00% |
| c) | Media Preparation | 5.00% |
| d) | acrylamides copolymer, mineral oil C13-C14 isoparaffin, polysorbate 85 | 3.00% |

Mixture a) is melted at approximately 70° C. and mixture b) is heated to approximately 70° C. and added to mixture a) while stirring. Stirring is continued until the lotion has cooled down to approximately 30° C. Then c) and d) are added while stirring, and the lotion is homogenized.

2) Gel-Lotion

| a) acrylamides copolymer, mineral oil, C13-14 isoparaffin, polysorbate 85 | 5.00% |
|---|---|
| myreth-3 myristate | 4.00% |
| b) water, distilled | 85.00% |
| phenoxyethanol (and) methylparaben (and) ethylparaben (and) butylparaben (and) propylparaben (and) isobutylparaben | 0.50% |
| xanthan gum | 0.50% |
| c) Media Preparation | 5.00% |

Mixture a) is dissolved at approximately 50° C. Mixture b) is dispersed at room temperature and added to a) while stirring. Then, composition c) is added while stirring.

3) Oil-In-Water Cream

| a) cetearyl alcohol (and) ceteareth-20 | 8.00% |
|---|---|
| cocoglycerides | 2.00% |
| cetearyl alcohol | 2.00% |
| dicaprylyl ether | 8.00% |
| oleyl erucate | 7.00% |
| phenoxyethanol, methylparaben, ethylparaben, butylparaben, propylparaben, isobutylparaben | 0.30% |
| b) water, distilled | 62.40% |
| phenoxyethanol, methylparaben, ethylparaben, butylparaben, propylparaben, isobutylparaben | 0.30% |
| glycerin | 5.00% |
| c) Media Preparation | 5.00% |

Mixture a) is melted at approximately 70° C. and mixture b) is heated to approximately 70° C. and added to mixture a) while stirring. Stirring is continued until the cream has cooled down to approximately 30° C. Then, composition c) is added while stirring and the cream is homogenized.

4) Water-In-Oil Cream

| a) diisostearoyl polyglyceryl-3 dimer dilinoleate | 3.00% |
|---|---|
| beeswax | 0.60% |
| castor oil, hydrated | 0.40% |
| paraffinum subliquidum | 5.00% |
| isohexadecane | 10.00% |
| PPG-15 stearyl ether | 2.00% |
| dimethicone | 0.50% |
| phenoxyethanol, methylparaben, ethylparaben, butylparaben, propylparaben, isobutyparaben | 0.30% |
| b) water, distilled | 68.40% |
| phenoxyethanol, methylparaben, ethylparaben, butylparaben, propylparaben, isobutylparaben | 0.30% |
| glycerin | 3.00% |
| $MgSO_4 \cdot 7H_2O$ | 1.00% |
| c) Media Preparation | 5.00% |
| d) silica dimethyl silylate | 0.50% |

Mixture a) is heated to approximately 80° C., mixture b) is brought to 80° C. and added to a) while stirring. Stirring is continued until the cream has cooled down to approximately 30° C., then c) and d) are added, and the cream is homogenized.

5) Shampoo

| Sodium polyoxyethylene lauryl ether sulfate | 15.0% |
|---|---|
| Alkyl polyglucoside | 4.0% |
| N-ethanol-N-methyl dodecanoic acid amide | 3.0% |
| EDTA-$Na_2$ | 0.3% |
| Malic acid to adjust pH to 6.0 q.s. | |
| Preservative | 0.5% |
| Media Preparation | 10.0% |
| Purified water balance | |
| Total | 100.0% |

All ingredients are mixed together and the volume is brought to about 90 ml. The pH is then adjusted and the volume is finally adjusted to 100 ml (all percentages are weight %).

6) Body Wash

| Sodium polyoxyethylene lauryl ether sulfate | 16.0% |
|---|---|
| Sodium polyoxyethylene | 5.0% |
| N-ethanol-N-methyl palm kernel oil fatty acid amide | 2.5% |
| Glycerin | 3.0% |
| Cationized cellulose | 0.1% |
| Ethylene glycol distearate | 3.0% |
| EDTA-$Na_2$ | 0.3% |
| Citric acid to adjust pH to 5.7 q.s. | |
| Preservative | 0.5% |
| Media Preparation | 7.5% |
| Purified water balance | |
| Total | 100.0 |

All ingredients are mixed together and the volume is brought to about 90 ml. The pH is then adjusted and the volume is finally adjusted to 100 ml (all percentages are weight %).

7) Face Wash

| Sodium polyoxyethylene lauryl ether sulfate | 20.0% |
|---|---|
| N-ethanol-N-methyl dodecanoic acid amide | 4.8% |
| Glycerin | 3.0% |
| Hydroxyethyl cellulose | 0.3% |
| Ethylene glycol distearate | 1.5% |
| EDTA-$Na_2$ | 0.3% |
| Citric acid to adjust pH to 6.0 q.s. | |
| Preservative | 0.5% |
| Media Preparation | 10.0% |
| Purified water balance | |
| Total | 100.0 |

All ingredients are mixed together and the volume is brought to about 90 ml. The pH is then adjusted and the volume is finally adjusted to 100 ml (all percentages are weight %).

Example 8. Stimulation of Fibroblasts

An in vitro model can be employed to investigate mediated effects of stimulation of fibroblasts in which active ingredients (conditioned medium) stimulates/activates keratinocytes, and in which activated keratinocytes release molecules that stimulate fibroblasts in deep skin layers.

Experiment 1: Skin keratinocytes are plated at the top of porous membrane of a cell culture insert. Skin fibroblasts are seeded within three-dimensional (3D) extracellular matrix (ECM) containing collagen; the ECM with fibroblasts is attached to the bottom side of porous membrane as shown in FIG. 1. Thus, the whole system represents an in vitro 3D model of skin where keratinocytes form the top layer of the skin, and fibroblasts in ECM form the dermis. The active ingredients are then applied on the top of system (keratinocytes) and may activate keratinocytes that following activation may affect/activate fibroblasts. Such system will allow testing of multiple effects of active ingredients on skin cells in the 3D environment.

Figure 2:
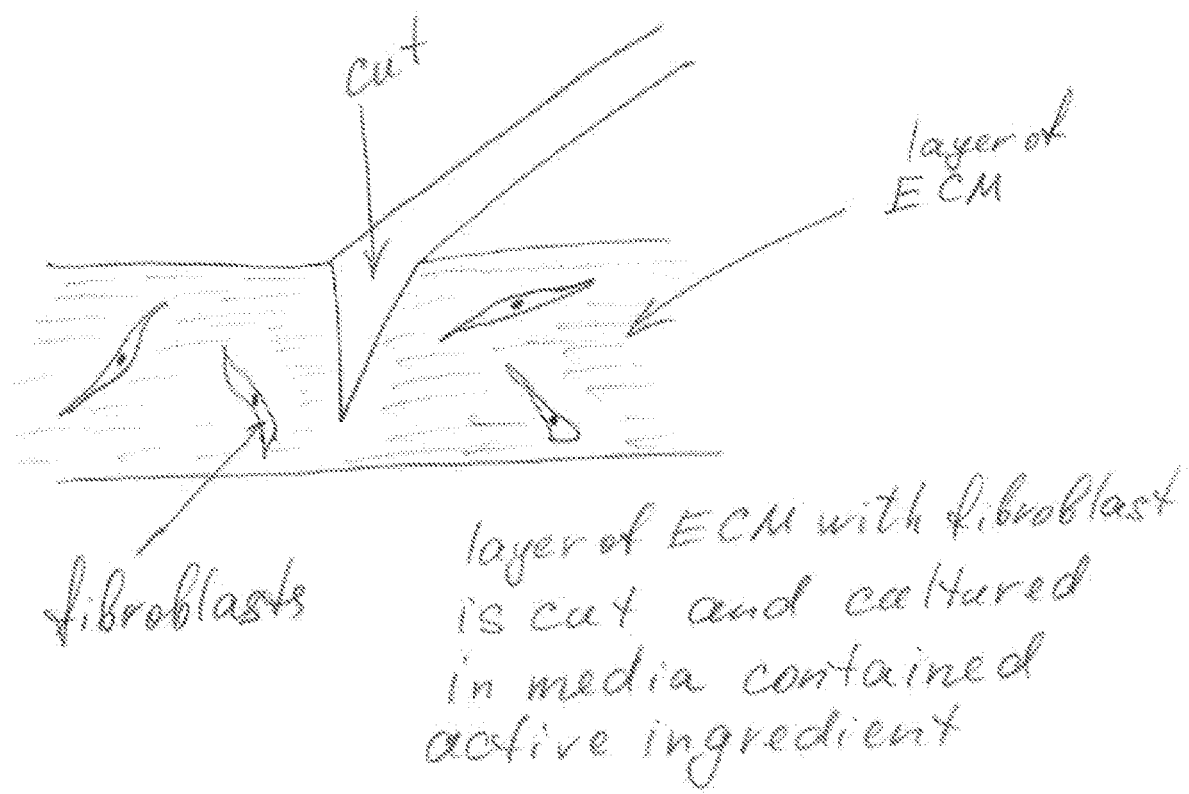
FIG. 2 is another schematic illustration of a cell culture to investigate effects of conditioned medium.

Experiment 2: Skin fibroblasts are seeded within a thick layer of three-dimensional (3D) extracellular matrix (ECM) containing collagen. The ECM with fibroblasts is cut ('wounded') and then cultured with media containing active ingredients. The speed and quality of in vitro wound healing is then evaluated (the effect of active ingredients on the dermis healing) as schematically illustrated in FIG. 2.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refers to at least one of something selected from the group consisting of A, B, C . . . and N, the text should be interpreted as requiring only one element from the group, not A plus N, or B plus N, etc.

What is claimed is:

1. A method of treatment of skin of a mammal in need thereof, wherein the skin is affected with a skin condition, comprising:
    generating a combined conditioned media preparation comprising a first set of growth factors and a second set of growth factors by initiating a cell culture by contacting a cell culture media with a cell population consisting of a plurality of pluripotent stem cells;
    initiating differentiation of the plurality pluripotent stem cells by adding a differentiation media to the cell culture to induce differentiation of pluripotent stem cells of the cell culture, thereby generating a differentiating stem cell culture;
    incubating the differentiating stem cell culture until a first time point, wherein differentiation of the plurality of pluripotent stem cells generates a first distinct cell population consisting of cells a first distinct cell type that are in a first distinct differentiation state at the first time point;
    collecting a first conditioned media comprising the first set of growth factors from the differentiating stem cell culture at the first time point;
    storing the first conditioned media;
    adding a volume of the differentiating media to the differentiating stem cell culture;
    collecting a second conditioned media from the differentiating stem cell culture at a second time point following addition of the differentiating media, wherein cells of differentiating stem cell culture consisting of cells of a second distinct cell type that are in a second differentiation state at the second time point;
    combining the first conditioned media and the second conditioned media to generate the combined conditioned media; and
    topically administering a composition comprising the combined conditioned media and a pharmaceutically or cosmetically acceptable carrier suitable for topical administration in an amount and under a protocol effective to treat the condition.

2. The method of claim 1 wherein the skin condition is a mechanical trauma, irradiative injury, or scarring.

3. The method of claim 1 wherein the first and second media are enclosed in the composition in a nanoparticle.

4. The method of claim 1 wherein the amount and protocol are effective to at least one of stimulate cell migration, stimulate or reconstruct skin collagen structure, stimulate cell redistribution in an affected area and surrounded tissue, inhibit apoptosis, stimulate angiogenesis, stimulate chemotaxis, stimulate an immune response, and stimulate repair of a cell membrane.

5. The method of claim 1, wherein the pluripotent stem cells are adult stem cells.

6. The method of claim 1, wherein the pluripotent stem cells are embryonic stem cells.

7. The method of claim 1, wherein the pluripotent stem cells are induced pluripotent stem cells.

8. The method of claim 1, wherein the pluripotent stem cells are mesenchymal stem cells.

9. The method of claim 1, wherein the pluripotent stem cells are neural stem cells.

10. The method of claim 1, wherein the pluripotent stem cells are human parthenogenetic stem cells.

* * * * *